United States Patent
Bertagnon

(10) Patent No.: US 10,245,123 B2
(45) Date of Patent: Apr. 2, 2019

(54) METHOD FOR MANUFACTURING A DENTAL PROSTHESIS

(71) Applicant: DENTAL KNOWLEDGE S.r.l., Milan (IT)

(72) Inventor: Valter Bertagnon, Milan (IT)

(73) Assignee: Dental Knowledge S.R.L. (IT)

( * ) Notice: Subject to any disclaimer, the term of this patent is extended or adjusted under 35 U.S.C. 154(b) by 380 days.

(21) Appl. No.: 14/910,762

(22) PCT Filed: Sep. 23, 2014

(86) PCT No.: PCT/IB2014/064761
§ 371 (c)(1),
(2) Date: Feb. 8, 2016

(87) PCT Pub. No.: WO2015/044862
PCT Pub. Date: Apr. 2, 2015

(65) Prior Publication Data
US 2016/0184061 A1      Jun. 30, 2016

(30) Foreign Application Priority Data
Sep. 23, 2013  (IT) ............... MI2013A1561

(51) Int. Cl.
*A61C 8/00* (2006.01)
*B23Q 3/10* (2006.01)
(Continued)

(52) U.S. Cl.
CPC ...... *A61C 13/0022* (2013.01); *A61C 13/0006* (2013.01); *A61C 13/083* (2013.01); *B23Q 3/103* (2013.01); *A61C 8/005* (2013.01)

(58) Field of Classification Search
CPC ............ A61C 13/0003; A61C 13/0006; A61C 13/0009; A61C 13/0022; A61C 13/34; A61C 8/005; A61C 8/0054; B23Q 3/103
See application file for complete search history.

(56) References Cited

U.S. PATENT DOCUMENTS 4,627,136 A * 12/1986 Kreylos ............. A61C 13/0003
                                              219/69.17
5,475,912 A * 12/1995 Sundstrom ......... A61C 13/0003
                                              29/896.1
(Continued)

FOREIGN PATENT DOCUMENTS

EP     1481647 A1   12/2004
JP     2007222225 A   9/2007
(Continued)

OTHER PUBLICATIONS

English Translation of JP 2007222225 A.*
(Continued)

*Primary Examiner* — Jason L Vaughan
(74) *Attorney, Agent, or Firm* — Waller Lansden Dortch & Davis, LLP; Matthew C. Cox

(57) ABSTRACT

This invention concerns a manufacturing method of a dental prosthesis, with specific reference to single-tooth prostheses. In particular, this invention deals with a manufacturing method a dental prosthesis or part thereof, that includes a milling step of a block (1) made of a material suitable for dental uses, where the aforementioned block (1) is secured to a connection device (L) with a dental implant.

9 Claims, 3 Drawing Sheets

(51) Int. Cl.
*A61C 13/00* (2006.01)
*A61C 13/083* (2006.01)

(56) References Cited

U.S. PATENT DOCUMENTS

| | | | | |
|---|---|---|---|---|
| 5,813,859 | A * | 9/1998 | Hajjar | A61C 13/0003 29/896.1 |
| 6,991,853 | B2 * | 1/2006 | Branco de Luca | A61C 13/0003 428/542.8 |
| 7,234,938 | B2 * | 6/2007 | Bodenmiller | A61C 13/0004 433/51 |
| 8,057,912 | B2 * | 11/2011 | Basler | A61C 13/0003 428/542.8 |
| 8,402,624 | B2 * | 3/2013 | Galehr | A61C 13/0022 29/281.1 |
| 8,425,973 | B2 * | 4/2013 | Dunne | A61C 13/0004 118/500 |
| 8,443,502 | B2 * | 5/2013 | Galehr | A61C 13/0022 29/281.1 |
| 8,769,822 | B2 * | 7/2014 | Warden | A61C 13/0004 29/896.1 |
| 8,844,139 | B2 * | 9/2014 | Johnson | A61C 13/0004 29/896.1 |
| 9,615,902 | B2 * | 4/2017 | Miguel | A61C 13/0006 |
| 9,937,024 | B2 * | 4/2018 | Steger | A61C 13/0022 |
| 2004/0120781 | A1 * | 6/2004 | Luca | A61C 13/0004 409/84 |
| 2006/0168815 | A1 * | 8/2006 | Saliger | A61C 13/0022 29/896.11 |
| 2008/0108014 | A1 * | 5/2008 | Holzner | A61C 13/0027 433/163 |
| 2012/0251979 | A1 * | 10/2012 | Karim | A61C 8/005 433/201.1 |
| 2014/0162210 | A1 * | 6/2014 | Thomke | A61C 8/0012 433/167 |
| 2015/0017604 | A1 * | 1/2015 | Kern | A61C 8/005 433/173 |
| 2015/0093719 | A1 * | 4/2015 | Beeby | A61C 13/0013 433/202.1 |

FOREIGN PATENT DOCUMENTS

| | | |
|---|---|---|
| WO | 2011056452 A2 | 5/2011 |
| WO | 2013174521 A2 | 11/2013 |

OTHER PUBLICATIONS

JP 2007222225 A—English Translation.*
International Search Report dated Dec. 18, 2014 in corresponding PCT Patent Application No. PCT/IB2014/064761 filed Sep. 23, 2014.
Written Opinion dated Dec. 18, 2014 in corresponding PCT Patent Application No. PCT/IB2014/064761 filed Sep. 23, 2014.

* cited by examiner

METHOD FOR MANUFACTURING A DENTAL PROSTHESIS

FIELD OF THE INVENTION

This invention concerns a manufacturing method of a dental prosthesis, with specific reference to single-tooth prostheses.

BACKGROUND ART

A dental implant consists of a screw made of a biocompatible material, typically titanium, coated, if need be, with additional substances aimed at enhancing adhesion, osseointegration and resistence to bacterial attacks. The implant consists of an upper portion designed to emerge from the gingival arch that includes an internal thread to fix a connection device to which the dental crown will be secured.

FIG. 1A shows one of the said connection devices L on which a stump M will be positioned, based on the conventional technique. The crown C will be then secured to the aforementioned stump M, as displayed in FIG. 1C. Both the stump M and the crown C are typically realized with materials that are suitable for dental uses. The procedure is first based on injecting some ceramic material within a mold, reproducing the shape of the stump and/or the crown, followed by baking in an oven, finishing off and polishing.

The foregoing procedure is carried out in a dental laboratory, equipped with the necessary equipments and endowed with the required skills.

Once this procedure has been completed, the realized prosthesis or the stump are glued to the connection device L and the whole work will be finally assembled with the dental implant, already positioned in the patient's oral cavity.

The procedure described above, besides being highly demanding in terms of high technical skills, is long and laborious and the patient is obliged to undergo several dental sessions, with significant time intervals between the moment when the dentist obtains the impression and the moment when the dental technician realizes the prosthesis.

Recently, new techniques have been spreading: the latter in turn are based on CAD/CAM system prosthesis design as well as on milling machine-assisted manufacturing, wherein the said milling machines are installed either in a dental laboratory or in a dental surgery. However, the realization of the stump M to be assembled with the connection device L still has to be carried out following the traditional system described above.

It would thus be desirable to enhance the realization procedure of a dental prosthesis in such a way that its manufacturing, or at least part thereof, is carried out directly in the dental surgery, with no need of a dental technician's specific skills. In this way, indeed, the manufacturing time could be significantly reduced, thus decreasing the number of dental sessions the patient has to undergo.

SUMMARY OF THE INVENTION

The problem addressed by the present invention is that of providing a procedure to meet the goal described above.

The said problem is solved through a manufacturing method of a dental prosthesis or a part thereof, as highlighted in the attached claims, whose definitions constitute integral part of this description.

An object of the invention is thus a manufacturing method of a dental prosthesis, or a part thereof, easy and that does not require very high technical skills.

A further object of the invention is a coupling member between a milling machine and the connection device of a dental implant.

Additional features and advantages of the present invention will emerge from the description of some realization examples carried out here below for illustrative, yet non limitative purposes, with specific reference to the annexed figures.

DETAILED DESCRIPTION OF THE INVENTION

Figure 1A:
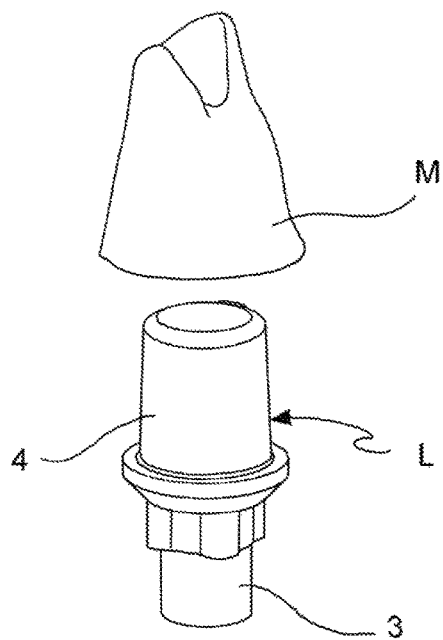
FIG. 1A represents an exploded perspective view of the stump of a dental prosthesis as well as of a connection element with a dental implant, according to the current state of art.
Figure 1B:
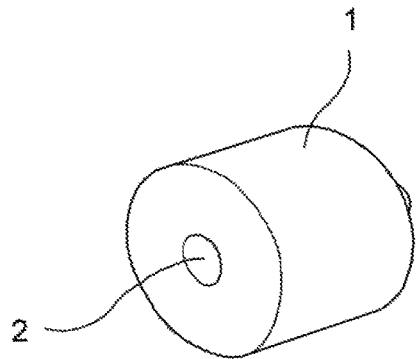
FIG. 1B shows a perspective view of a small block of ceramic material for dental use.

The invention concerns a manufacturing method of a dental prosthesis or a part thereof, that includes a milling step of a small block 1 made of a material suitable for dental uses, wherein the said block 1 is secured to a connection element for a dental implant.

According to a preferred embodiment, the method of the invention includes the following steps:
providing a milling machine 7 for dental uses,
supplying a block 1 made of a material suitable for manufacturing dental prosthesis provided with a hole 2,
providing a connection element L for a dental implant, the said connection element L having a first connection portion 3 to the said dental implant and a second connection portion 4 to a dental prosthesis,
inserting the said second connection portion 4 of the connection element L into the hole 2 of the block 1 and securing the former to the latter, so as to form an assembly block 1—connection element L,
providing a coupling member 5 between the said first connection portion 3 and the supporting element 6 of the said milling machine 7,
connecting the assembly block 1—connection element L of step d) to the coupling member 5,
assembling the coupling member 5 with the assembly block 1—connection element L on the supporting element 6 of the said milling machine 7,
milling the said block 1, so as to obtain either a stump M or a dental prosthesis.

The milling machine 7 is of a conventional type.

Milling machines of this kind are sold by firms like, for instance, Sirona or KaWo. The milling machine 7 includes a supporting element 6, on which the part to be milled is mounted, and a milling spindle 8, on which a suitable end mill cutter 9 is put. Milling machines of this type can work automatically, based on a CAD/CAM-elaborated working project.

The block 1 can be realized in any material suitable for manufacturing dental prosthesis. The said material is typically a ceramic material, like for instance disilicate or feldspathic ceramic, zirconium oxide, glass-ceramic, composite etc.

In certain embodiments, a nanocomposite ceramic material is used. The said material is a hybrid ceramic with dual network structure, microfine structure (86% by weight) and reinforced through a poly-acrylate network; it combines the advantages of ceramic together with those of composite resins.

These kinds of materials are directly produced in their definitive state and consequently do not need additional baking processes; they can thus be used to realize dental prostheses with definitive morphology and are millable in the dental surgery, starting from the block 1.

Vice versa, when using the other ceramic materials listed above, additional steps of sintering or superficial coloring with heating processes are required, increasing the number of scheduled dental sessions. The neck K (FIG. 1C), representing the visible part of the stump M obtained after milling the small block 1B, instead, can be manually polished by the dental technician in a dental laboratory.

Bin certain embodiments, the block 1 has a cylindrical shape and presents a longitudinal through hole 2.

Figure 1C:
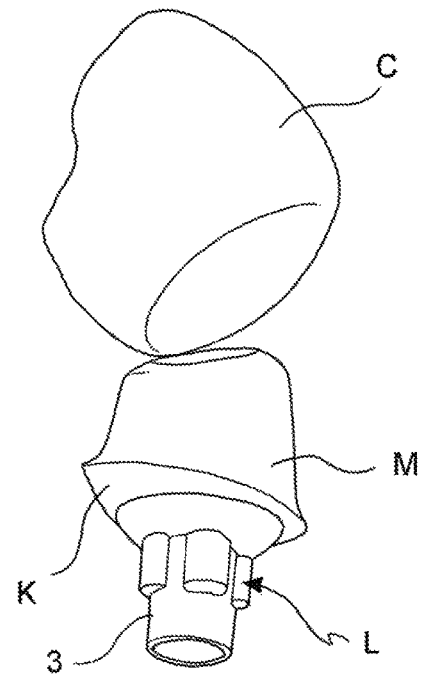
FIG. 1C displays an exploded perspective view of an assembly made up of a connection element, a stump and a crown.
Figure 2:
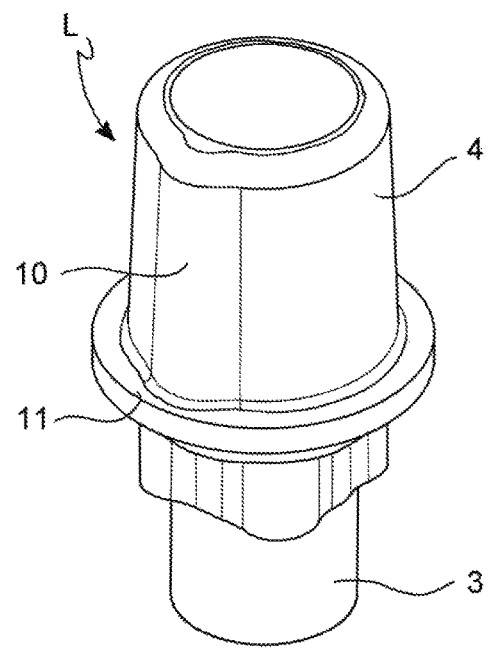
FIG. 2 represents a perspective view of a connection element between a small block of ceramic material for dental use and a dental implant.
Figure 3:
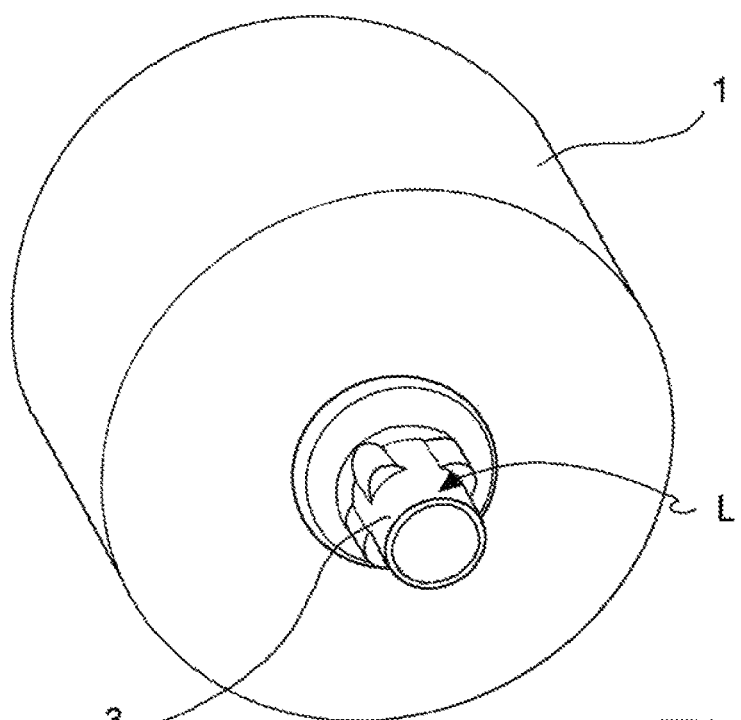
FIG. 3 shows a perspective view of the assembly made up of a small ceramic block as well as of a connection element to a dental implant used in the manufacturing method of the invention.

The connection element L, displayed in FIG. 2, includes a first connection portion 3 to a dental implant and a second connection part 4 either to an abutment or to a crown with definitive anatomy. The first connection portion 3 has a varying shape, depending on the used dental implant type. The shape shown in FIGS. 1A and 2 is merely indicative. Different types of connection elements L, also called "link" or "abutment", are thus available on the market.

The second connection portion 4 has a slightly conical shape and comprises a longitudinal relief 10, serving as a reference positioning mark either for the stump or for the crown to be glued.

A flange 11 is located between the first 3 and the second connection parts, so that its lower portion matches with the dental implant, whereas its upper section acts as end limit for the block 1.

The fixing of the second connection portion 4 of the connection element L into the hole 2 of the block 1 is carried out through gluing. Typically used glues are, for instance, self and light-cured ionomer cements.

Figure 4:
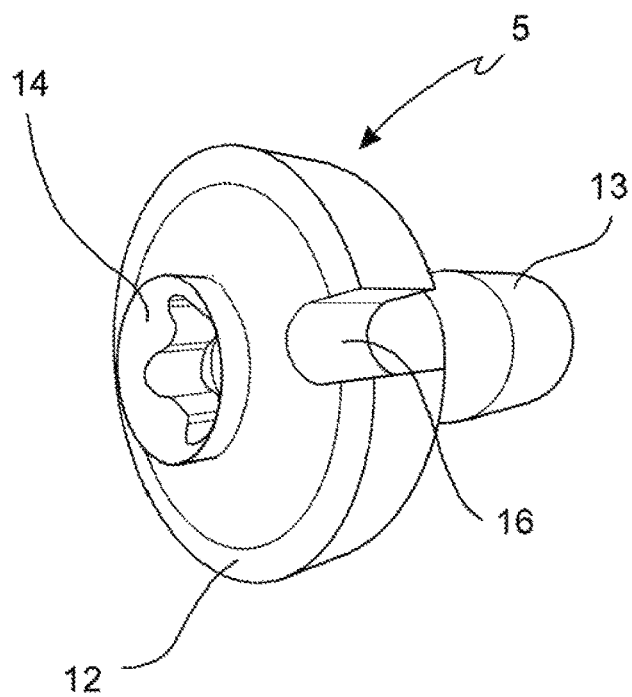
FIG. 4 displays a perspective view of a coupling member between the assembly described in FIG. 3 and a milling machine, exploitable in the inventive method.
Figure 5:
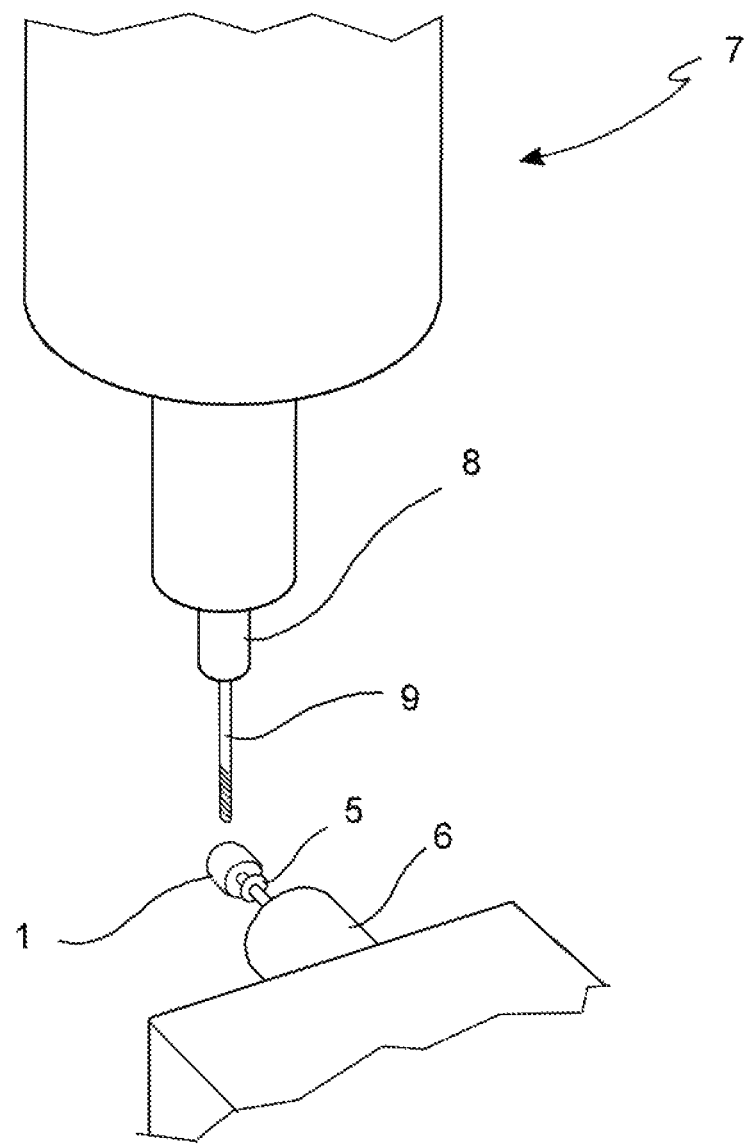
FIG. 5 represents a partial view of a milling machine for dental uses, applicable to the manufacturing method of the invention.

With reference to FIG. 4, the coupling member 5 comprises a first matching portion 12 with the first connection portion 3 of the connection element L as well as a second coupling portion 13 with the supporting element 6 of the milling machine 7.

The first matching portion 12 includes a seat 14 to contain the first connection portion 3 of the connection element L. The foregoing seat thus has a shape that is substantially equivalent to the seat of the dental implant the connection element L is destined to. For this reason, the shapes both of the seat 14 and of the second coupling portion 13 shown in the figure are only indicative and vary depending on the type of connection element L(varying, in turn, based on the type of dental implant) and of milling machine 7 that are used, respectively.

A cavity 16 is located on the edge of the first matching portion 12. The cavity 16 is used to position the assembly block 1—connection element L, matched with the coupling member 5, with the proper rotation on the supporting element 6 of the milling machine 7, thus acting as a reference mark.

The coupling member 5 can be realized as a single piece, wherein the shape of the second coupling portion 13 depends on the milling machine type, whereas the shape of the seat 14 depends on the brand as well as on the type of dental implant that has been used. The block 1 will be secured to the coupling member 5 by a through screw tightened, in turn, with a nut that will block the assembly and will fasten it from the back part of the coupling portion 13. With this respect, a kit including a series of coupling members 5, depending on the brands both of the implant and of the milling machine, and a set of blocks 1, varying based on the implant's brand and measure and with different colors, could be provided.

The first matching portion 12 includes a cavity 16 along its edge. The cavity 16 is used to position the assembly block 1—connection element L matched and screwed with the coupling member 5 with the proper rotation into the milling machine plate, as the cavity gets stuck on a pivot located on the milling machine plate.

The method this invention refers to thus allows to obtain a stump, a crown or a complete dental prosthesis through milling, directly in the dental surgery equipped with the milling machine. The CAD-designed abutment will have a well-known, precise shape; following the very same project crown manufacturing will also be possible, in such a way that the latter will match the abutment precisely and all this can be achieved in only one dental session. In this way, the manufacturing and the installation of a dental prosthesis within a patient's mouth are heavily simplified and the patient's discomfort is reduced correspondingly, due to the lower number of dental sessions he has to undergo.

Clearly enough, only a few particular embodiments of the present invention have been described so far: a skilled person will be able to make all the necessary changes to adapt it to particular applications, with no prejudice of the scope of protection of this invention.

The invention claimed is:

1. A method for manufacturing a dental prosthesis or a part thereof, comprising a milling step of a block realized in a material suitable for dental uses, wherein the block is secured to a connection element with a dental implant, comprising the following steps:
   a) providing a milling machine having a supporting element;
   b) supplying the block made of a material suitable for manufacturing the dental prosthesis, the block provided with a hole;
   c) providing the connection element for the dental implant, the connection element having a first connection portion operable to connect to the dental implant, and a second connection portion operable to connect to the dental prosthesis;
   d) inserting the second connection portion of the connection element into the hole of the block and securing the second connection portion to the block, so as to form an assembly block-connection element;
   e) providing a coupling member between the first connection portion and the supporting element of the milling machine;
   f) connecting the assembly block-connection element to the coupling member;

g) assembling the coupling member with the assembly block-connection element on the supporting element of the milling machine, wherein the second connection portion of the connection element has a substantially conical shape and comprises a longitudinal relief;

h) milling the block, so as to obtain a stump or the dental prosthesis.

2. The method according to claim 1, wherein the block is made of a ceramic material.

3. The method according to claim 2, wherein the ceramic material is selected from disilicate ceramic, zircomum oxide, glass ceramic and a nanocomposite ceramic material.

4. The method according to claim 1, wherein the block has a cylindrical shape and has a longitudinal through hole.

5. The method according to claim 1, wherein the second connection portion of the connection element is secured into the hole of the block by gluing.

6. The method according to claim 1, wherein the coupling member comprises a first matching portion with the first connection portion of the connection element, and a second matching portion with the supporting element of the milling machine.

7. The method according to claim 6, wherein the first matching portion comprises a seat to contain the first connection portion of the connection element, said seat having a shape that is substantially equivalent to a second seat of the dental implant.

8. A method for manufacturing a dental prosthesis or a part thereof, comprising a milling step of a block realized in a material suitable for dental uses, wherein the block is secured to a connection element with a dental implant, comprising the following steps:

a) providing a milling machine having a supporting element;

b) supplying the block made of a material suitable for manufacturing the dental prosthesis, the block provided with a hole;

c) providing the connection element for the dental implant, the connection element having a first connection portion operable to connect to the dental implant, and a second connection portion operable to connect to a dental prosthesis;

d) inserting the second connection portion of the connection element into the hole of the block and securing the second connection portion to the block, so as to form an assembly block-connection element;

e) providing a coupling member between the first connection portion and the supporting element of the milling machine, wherein the coupling member comprises a first matching portion with the first connection portion of the connection element, and a second matching portion with the supporting element of the milling machine;

f) connecting the assembly block-connection element to the coupling member;

g) assembling the coupling member with the assembly block-connection element on the supporting element of the milling machine;

h) milling the block, so as to obtain a stump or a dental prosthesis.

9. The method according to claim 8, wherein the first matching portion comprises a seat to contain the first connection portion of the connection element, said seat having a shape that is substantially equivalent to a second seat of the dental implant.

\* \* \* \* \*